US00PP29464P2

(12) United States Plant Patent
Fox et al.

(10) Patent No.: US PP29,464 P2
(45) Date of Patent: Jul. 3, 2018

(54) ***TIARELLA* PLANT NAMED 'GOWING'**

(50) Latin Name: ***Tiarella* hybrid**
Varietal Denomination: GOWING

(71) Applicants: Vicky Fox, Cheshire (GB); Richard Fox, Cheshire (GB)

(72) Inventors: Vicky Fox, Cheshire (GB); Richard Fox, Cheshire (GB)

( * ) Notice: Subject to any disclaimer, the term of this patent is extended or adjusted under 35 U.S.C. 154(b) by 0 days.

(21) Appl. No.: 15/330,013

(22) Filed: Jul. 25, 2016

(51) Int. Cl.
*A01H 5/02* (2018.01)

(52) U.S. Cl.
USPC ..... Plt./486

(58) Field of Classification Search
USPC ..... Plt./486
CPC ..... A01H 5/02; A01H 5/12; A01H 5/00
See application file for complete search history.

(56) References Cited

U.S. PATENT DOCUMENTS

PP12,397 P2 * 2/2002 Heims ..... A01H 5/02
Plt./486

OTHER PUBLICATIONS

Rice Chelsea Flower Show: Plant of the Year revealed May 19, 2015, retrieved on Sep. 12, 2017, retrieved from the Internet at http://www.telegraph.co.uk/gardening/chelseaflowershow/11614990/Chelsea-Flower-Show-Plant-of-the-Year-revealed.html 5 pp. (Year: 2015).*
Upov Pluto Plant Variety Database Sep. 9, 2017 *Tiarella* Gowing, retrieved on Sep. 12, 2017, retrieved from the Internet at https://www3.wipo.int/pluto/user/en/index.jsp 1 page (Year: 2017).*

* cited by examiner

*Primary Examiner* — June Hwu
(74) *Attorney, Agent, or Firm* — Penny J. Aguirre

(57) ABSTRACT

A new cultivar of *Tiarella* hybrid named, 'GOWING', that is characterized by its compact, upright plant habit, its pale pink buds that open to flowers that are white in color, and its deeply dissected, variegated foliage that is green in color with dark maroon centers and tri-lobed with an extra basal lobe.

2 Drawing Sheets

Botanical classification: *Tiarella* hybrid.
Cultivar designation: 'GOWING'.

BACKGROUND OF THE INVENTION

The present invention relates to a new and distinct cultivar of *Tiarella* of hybrid origin, botanically known as *Tiarella* and hereinafter referred to by its cultivar name 'GOWING'.

'GOWING' derived from an ongoing breeding program by the Inventors at their nursery in Cheshire, United Kingdom. One of the Inventors made a cross in 2011 between unnamed and unpatented proprietary plants in the Inventors breeding program as the female and male parents. The Inventors selected 'GOWING' in May of 2012 as a single unique plant amongst the seedlings that resulted from the above cross.

Asexual propagation of the new cultivar was first accomplished in spring of 2013 by one of the Inventors by in vitro propagation, initiated from meristem tissue, in Dundee, Scotland. Asexual propagation of the new cultivar by in vitro propagation has determined that the characteristics of the new cultivar are stable and are reproduced true to type in successive generations.

SUMMARY OF THE INVENTION

The following traits have been repeatedly observed and represent the characteristics of 'GOWING'. These attributes in combination distinguish 'GOWING' as a new and distinct cultivar of *Tiarella*.

1. 'GOWING' exhibits a compact, upright plant habit.
2. 'GOWING' exhibits pale pink buds that open to flowers that are white in color.
3. 'GOWING' exhibits deeply lobed, variegated foliage that is green in color with dark maroon centers.
4. 'GOWING' exhibits leaves that are tri-lobed with an extra basal lobe.

'GOWING' can be most closely compared to the *Tiarella* cultivars 'Sugar and Spice' (U.S. Plant Pat. No. 16,738) and 'Spring Symphony' (U.S. Plant Pat. No. 12,397). 'Sugar and Spice' differs from 'GOWING' in having a larger overall plant habit, in having flowering stems that are taller in height, in having foliage that is yellow-green in color with dark brown centers, in having lightly fragrant flowers, and in lacking the extra basal leaf lobe. 'Spring Symphony' differs from 'GOWING' in having a larger overall plant habit, in having taller flowering stems, in having lightly fragrant flowers, in having a less vigorous fall re-bloom, and in lacking the extra basal leaf lobe.

BRIEF DESCRIPTION OF THE DRAWINGS

The accompanying colored photographs illustrate the overall appearance and distinct characteristics of the new *Tiarella*. The photographs were taken of 3 year-old plants of 'GOWING' as grown at the Inventors nursery in one-liter and 3-liter containers in Cheshire, United Kingdom.

The photograph in FIG. 1 provides a side view of 'GOWING' in bloom.

Figure 1:
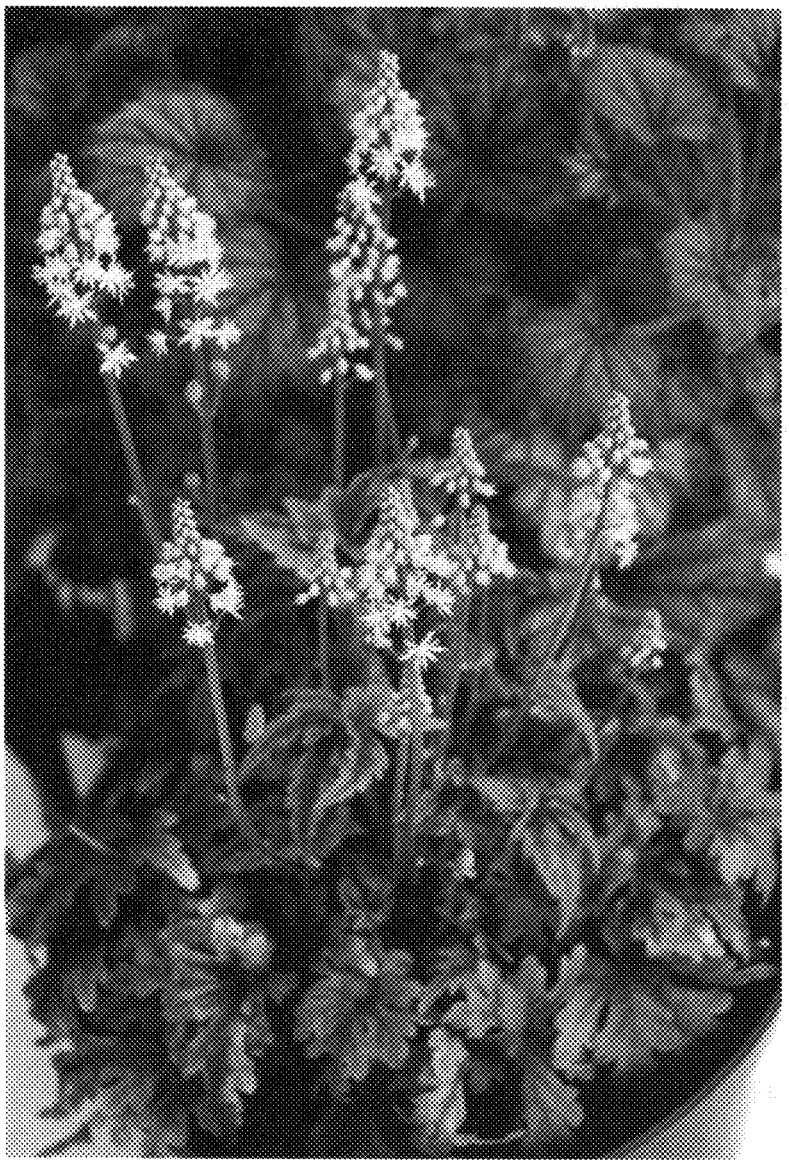
Figure 2:
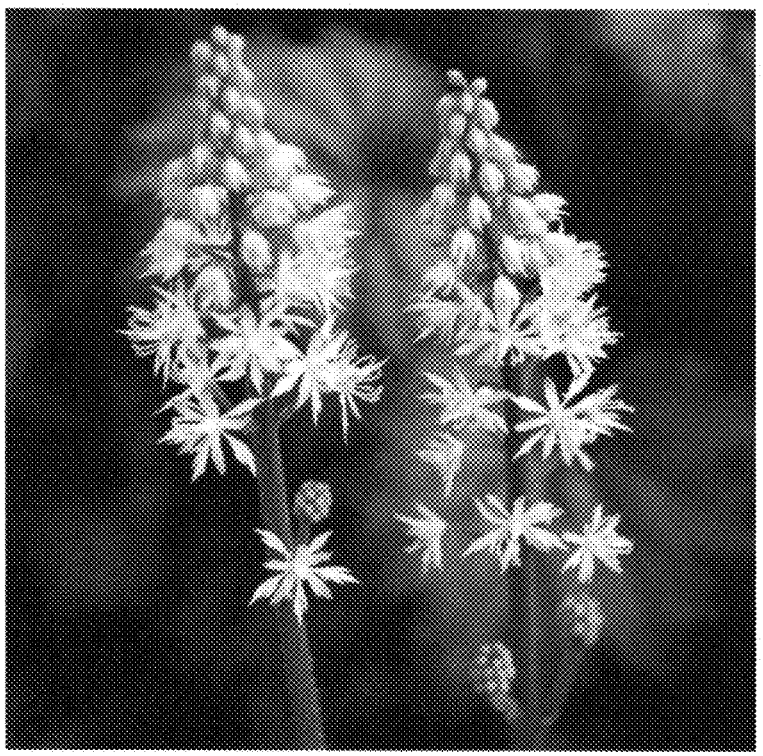

The photograph in FIG. 2 provides a close-up view of the inflorescences of 'GOWING'.

Figure 3:
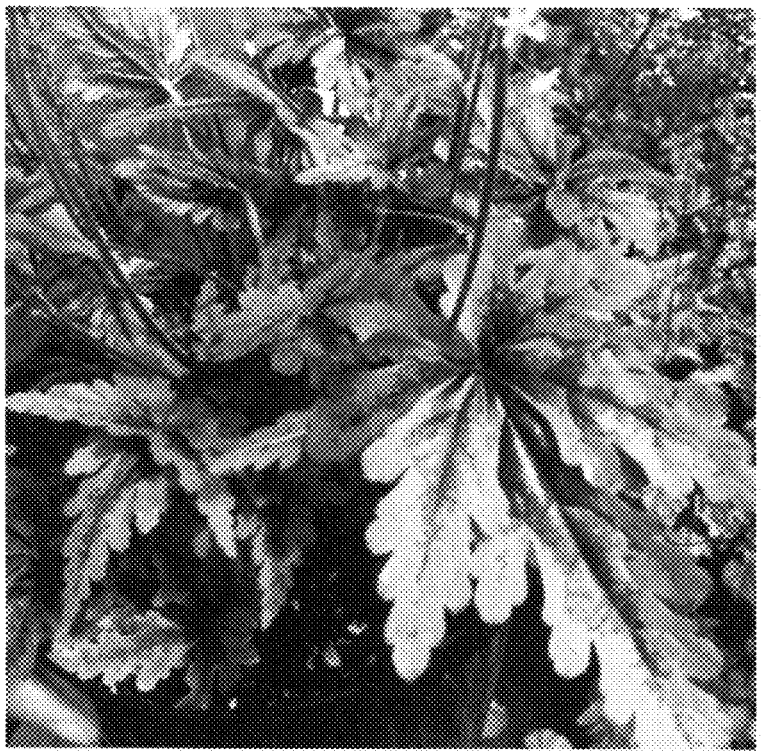

The photograph in FIG. 3 provides a close-up view of the foliage of 'GOWING'.

The colors in the photographs are as close as possible with the photographic and printing technology utilized and the color values cited in the detailed botanical description accurately describe the colors of the new *Tiarella*.

DETAILED BOTANICAL DESCRIPTION OF THE PLANT

The following is a detailed description of 3-year-old plants as grown at the Inventors nursery in 3-liter containers in Cheshire, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Blooming period*.—In April and May and again in September and October in Cheshire, United Kingdom.

*Plant type*.—Perennial, evergreen.

*Plant habit*.—Upright, compact, and clump-forming.

*Plant size*.—An average of 12 cm in height (without blooms), 23 cm in height (with blooms) and 20 cm in width.

*Hardiness*.—At least to U.S.D.A. Zone 6.

*Diseases and pests*.—Similar resistance and susceptibility to pests and diseases as other *Tiarella* varieties.

*Root description*.—Fibrous.

Growth and propagation:

*Growth rate*.—Moderate.

*Propagation type*.—In vitro propagation.

*Time required for root development*.—An average of six to 10 days for root initiation with a rooted plant in a one-liter container after about five weeks.

*Branching habit*.—Basal rosette.

Foliage description:

*Leaf shape*.—Ovate overall.

*Leaf division*.—Simple.

*Leaf margins*.—Tri-lobed with basal lobes deeply lobed into 2 lobes almost to base and an extra unique basal lobe (as illustrated in FIG. 3), lobes margins are crenate with serrations.

*Leaf apex*.—Acute.

*Leaf base*.—Cordate.

*Leaf aspect*.—Held horizontal to slightly upright to stem.

*Leaf size*.—An average of 6.2 cm in length and 5.7 cm in width.

*Leaf surface*.—Upper and lower surface slightly pubescent, with translucent hairs.

*Leaf arrangement*.—Basal clump.

*Leaf venation*.—Palmate, upper and lower surface; inconspicuous and the same color as the leaf surface.

*Leaf color*.—Immature; upper surface; N144B with centers N187A, lower surface N144A with centers 183C, mature; upper surface; 147A to 147B with centers N186B, lower surface; 148B with centers 183B, fading; upper and lower surface; 167B with centers 175A.

*Leaf attachment*.—Petiolate.

*Petiole*.—An average of 8.5 cm in length and 2 mm in diameter, color; young petiole 59A and mature petiole 146A, surfaces slightly pubescent, with translucent hairs.

Inflorescence description:

*Inflorescence type*.—Raceme of single, rotate flowers.

*Inflorescence size*.—An average of 4.5 cm in length and 2 cm in width.

*Flower quantity*.—An average of 40 to 60 blooms per raceme.

*Flower fragrance*.—Not present.

*Lastingness of flowers*.—Individual flowers an average 15 days, inflorescence an average of 40 days, self-cleaning.

*Flower arrangement*.—Terminal racemes.

*Flower aspect*.—Outwards.

*Flower size*.—An average of 5 mm in diameter length and 3 mm in width.

*Flower buds*.—Oval-campanulate in shape, about 5 mm in length and 2.5 mm in width, 186C to 186D in color.

*Calyx*.—An average of 4 mm in diameter and 3 mm in height.

*Petals*.—An average of 5, narrow elliptic to lanceolate in shape, an average of 4 mm in length and 0.75 mm in width, serrate margin with 1 to 3 jagged teeth towards the apex, acuminate apex, cuneate base, smooth surface, color; upper and lower surfaces when young 155B lightly tinged with 186D, upper and lower surfaces when mature 155B.

*Sepals*.—An average of 5, linear in shape, acute apex, fused base, entire margin, an average of 2 mm in length and 1 mm in width, 186B to 186C in color, pubescent surface covered with translucent hairs.

*Peduncles*.—Medium strong, an average of 19 cm in length and 2.5 mm in diameter, color; young 199A to 199B suffused with 187A, mature 199A to 199B, surface is slightly pubescent covered with translucent hairs.

*Pedicel*.—Medium strong, an average of 4.5 mm in length and 0.5 mm in width, pubescent surface, color 187B.

Reproductive organs:

*Gynoecium*.—1 pistil, 5 mm in length, stigma is capitate in shape and 155B in color, style is linear in shape widening towards the base, an average of 2 mm in length, less than 0.5 mm in width at the apex and 1 mm in width at the base, 155B in color, superior ovary is narrow conical in shape, an average of 1.5 mm in length and 1 mm in width, and 155B in color.

*Androecium*.—An average of 10 stamens (5 long and 5 short), basifixed anthers an average of 0.5 mm in length and less than 0.5 mm in width, ovoid in shape, and 28A to 28B in color, filaments an average of 1.5 mm in length and less than 0.5 mm in width, 155B very lightly tinged with 65D in color, pollen is moderate in quantity.

*Fruit/seeds*.—Ovoid in shape, an average of 1 mm in length and 0.5 mm in width, 200A in color.

It is claimed:

1. A new and distinct cultivar of *Tiarella* plant named 'GOWING' as herein illustrated and described.

* * * * *